US007798475B2

(12) United States Patent
Demirüker

(10) Patent No.: US 7,798,475 B2
(45) Date of Patent: Sep. 21, 2010

(54) DEVICE, METHOD AND USE FOR THE FORMATION OF SMALL PARTICLES

(75) Inventor: Mustafa Demirüker, Järfälla (SE)

(73) Assignee: Cens-Delivery AB (SE)

( * ) Notice: Subject to any disclaimer, the term of this patent is extended or adjusted under 35 U.S.C. 154(b) by 916 days.

(21) Appl. No.: 10/583,489

(22) PCT Filed: Dec. 20, 2004

(86) PCT No.: PCT/SE2004/001936

§ 371 (c)(1),
(2), (4) Date: Jun. 15, 2006

(87) PCT Pub. No.: WO2005/061090

PCT Pub. Date: Jul. 7, 2005

(65) Prior Publication Data

US 2007/0116650 A1 May 24, 2007

(30) Foreign Application Priority Data

Dec. 22, 2003 (SE) ................................ 0303476-6

(51) Int. Cl.
*B01F 3/04* (2006.01)

(52) U.S. Cl. ...................................... 261/78.2; 261/118

(58) Field of Classification Search ................ 261/78.2, 261/118
See application file for complete search history.

(56) References Cited

U.S. PATENT DOCUMENTS 3,885,918 A * 5/1975 Isahaya ...................... 422/168
4,011,290 A * 3/1977 Blomqvist et al. ............ 264/12
4,206,160 A * 6/1980 Suddendorf et al. ........ 261/78.2
4,284,590 A * 8/1981 DeBoer et al. ................ 261/62
5,232,164 A * 8/1993 Resch et al. ................ 239/434
5,411,208 A * 5/1995 Burgener ....................... 239/8
5,609,798 A * 3/1997 Liu et al. ................... 261/78.2
6,036,178 A * 3/2000 Nilsson ....................... 261/76
6,076,748 A * 6/2000 Resch et al. ............. 239/424.5
6,086,052 A * 7/2000 Rowe ........................ 261/18.1
2007/0164459 A1* 7/2007 Gottlieb et al. ............ 261/78.2

FOREIGN PATENT DOCUMENTS

WO WO 9836825 8/1998
WO WO 0103821 1/2001
WO WO 9501221 1/2001
WO WO 03008082 1/2003

OTHER PUBLICATIONS

International Search Report; PCT/SE2004/001936; Apr. 6, 2005.

* cited by examiner

*Primary Examiner*—Scott Bushey
(74) *Attorney, Agent, or Firm*—Cantor Colburn LLP

(57) ABSTRACT

The invention relates to a device for producing small particles of a certain substance. The device includes first inlet means (4) for a solution or a suspension containing the substance and second inlet means (3) for an atomizing agent. The device further includes mixing means (12) for the solution and the atomizing agent and outlet means (13) for the particles. First (9, 10) and second (14, 11) conduit means are provided from the first (4) and second (3) inlet means respectively to the mixing means (12). According to the invention the first (9, 10) and second (14, 11) conduit means meet each other at the mixing means (12) at an angle of at least 30°. The invention also relates to a corresponding method and to use of the device and the method as well as to particles obtained by the method.

33 Claims, 3 Drawing Sheets

DEVICE, METHOD AND USE FOR THE FORMATION OF SMALL PARTICLES

FIELD OF INVENTION

The present invention in a first aspect relates to a device for the formation of small particles of a certain substance, the device being of a kind including first inlet means for a solution or a suspension containing the substance, second inlet means for an atomizing agent, mixing means for mixing said solution and said atomizing agent, outlet for the particles, first conduit means from the first inlet means to the mixing means, and second conduit means from the second inlet means to the mixing means, which first and second conduit means meet each other at the mixing means at an angle of at least 30°.

In a second aspect the present invention relates to a method for the formation of such particles, the method including the steps of supplying a jet of an atomizing agent to a mixing area, supplying a liquid jet of a solution or a suspension containing the substance to the mixing area and withdrawing the jet of the particles from the mixing area, the jet of the atomising agent and the liquid jet being supplied such that they meet each other in the mixing area at an angle in the range of 30° to 150°.

The solution or suspension with the substance is a vehicle system for the substance, and the atomizing agent functions as an anti-solvent.

In further aspects the invention relates to the use of the invented device or the invented method for producing such particles as well as to particles obtained by the invented device or the invented method.

In this application small particles means particles of a size less than 10 µm, and in particular less than 1 µm. Further, by particle size of a batch of particles (powder) in this application is ment the size of a medium particle, i.e. particle such that in 50% by weight of the powder the particles are larger and in 50% by weight smaller.

BACKGROUND OF THE INVENTION

In particle forming processes there has been developed methods using supercritical fluids. Three types of these methods can be distinguished:

Rapid Expansion of Supercritical Solutions (RESS): This process consists in solvating the solute in the supercritical fluid and rapidly depressuring this solution through an adequate nozzle, causing an extremely rapid nucleation of the compound into a highly dispersed material. This process is attractive due to the absence of organic solvent use but is restricted to compounds with a reasonable solubility in the supercritical fluid.

Gas-Anti-Solvent precipitation (GAS), or Supercritical fluid Anti-Solvent: The processes generally comprise a solute dissolved in a conventional solvent called the vehicle system (solute+solvent). The vehicle is extracted by the supercritical fluid whereby extraction and droplet formation occurs simultaneously.

Modification of GAS: ASES—This name is rather used when micro-or nano-particles are expected. The process consists of pulverizing a solution of the solute in an organic solvent into a vessel swept by a supercritical fluid SEDS (Solution Enhanced Dispersion by Supercritical fluids)—This is a specific implementation of ASES and consists of co-introducing the vehicle with a flow of supercritical fluid in a mixing chamber in the spraying nozzle.

In all these processes it is important to maintain control over the working conditions especially the pressure. To be able to eliminate pressure fluctuations is vital for obtaining the desired particle size and size distribution as well as avoiding agglomeration.

A supercritical fluid can be defined as a fluid at or above its critical pressure and critical temperature simultaneously. The use of supercritical fluids and the properties thereof is described e.g. in J. W. Tom and P. G. Debendetti "Particle Formation with Supercritical Fluids—A Review", J. Aerosol Sci 22 (50. 554-584 (1991). Such fluids are interesting in particle formation since their solving power of different substances undergoes large changes as a result of changes in the physical characteristics of the surroundings, which characteristics can be relatively easily controlled, such as pressure. This property make supercritical fluid a medium highly appreciated for having a solving power being controllable by pressure and temperature changes, which is particularly useful in extraction and atomization of different substances, such as substances used in pharmacy. Further, supercritical fluids are normally gases under ambient condition, which eliminates the evaporation step needed in conventional liquid extraction.

In document WO 95/01221 the nozzle is designed for co-introduction of the vehicle and the supercritical fluid into the particle formation vessel. The nozzle has coaxial passages to carry the flow of the vehicle system and of the super-critical flow. The two are mixed in a particle formation chamber which is conical at an angle of taper typically in the range of 10 to 50 degrees. An increase in the angle may be used for increasing the velocity of the supercritical fluid introduced into the nozzle and hence the amount of physical contact between the supercritical fluid and the vehicle system. Control of parameters such as size and shape in the resulting product will be dependent upon variables including the flow rates of the supercritical fluid and/or the vehicle system, the concentration of the substance in the vehicle system, the temperature and pressure inside the particle formation vessel and the nozzle orifice diameter.

A further step to intensify the mixing between the vehicle system and the supercritical fluid in a mixing chamber is described in the document WO 00/67892. In this invention turbulence is introduced in at least one of the fluid gas or the vehicle system so as to create a controlled disorder in the flow of at least one of the fluid gas or vehicle system in order to control the particle formation in the mixing chamber.

In another patent document, WO96/00610, the method is improved by introducing a second vehicle, which is both substantially miscible with the first vehicle and substantially soluble in the supercritical fluid. The corresponding apparatus is consequently provided with at least three coaxial passages. These passages terminate adjacent or substantially adjacent to one another at the outlet end of the nozzle, which end is communicating with a particle formation vessel. In one embodiment of the nozzle the outlet of at least one of the inner nozzle passages is located a small distance upstream (in use) of the outlet of one of its surrounding passages. This allows a degree of mixing to occur within the nozzle between the solution or suspension, that is the first vehicle system, and the second vehicle. This pre-mixing of the solution and the second vehicle does not involve the supercritical fluid. It is in fact believed that the high velocity supercritical fluid emerging from the outer passage of the nozzle causes the fluids from the inner passages to the broken up into fluid elements. From these fluid elements the vehicles are extracted by the supercritical fluid, which results in the formation of particles of the solid previously solved in the first vehicle. The useful maximal taper of the conical end is in this document also augmented up to 60 degrees.

Another technique for particle precipitation using near-critical and super-critical antisolvents has later been described in WO97/31691. This document mentions the use of specialized nozzles for creating extremely fine droplet sprays of the fluid dispersions. The method involves passing the fluid dispersion through a first passageway and a first passageway outlet into a precipitation zone, which contains an antisolvent in near- or supercritical condition. Simultaneously an energizing gas stream is passed along and through a second passageway outlet proximal to the first fluid dispersion outlet. The passage of the energizing gas stream generates high frequency waves of the energizing gas adjacent to the first passageway outlet in order to break up the fluid dispersion into small droplets WO 03/008082 discloses a device where the first and second conduit means meet each other at the mixing means at an angle of about 90°. The two jets coming from the conduits meet each other in a free open space.

Other examples of devices and methods in this field are disclosed in WO98/36825, WO99/44733, WO99/59710, WO99/12009, WO01/03821, WO01/15664, WO02/38127, WO95/01221, WO01/03821, WO98/36825, PCT GB2003/001665 and PCT GB2003/001747.

Prior art of producing small particles by use of supercritical fluids as anti-solvents try to achieve control over pressure, temperature and flow in order to control morphology, size and size-distribution of the particles formed. The need from e.g. the pharmaceutical industry for small particles with desired size distribution and morphology do, however, invoke the need for better particle formation techniques than those mentioned in the disclosed prior art. This is of particular interest in creating particles in the nanometer size range. Commonly encountered problems with existing particle formation designs (nozzle designs) are clogging of the opening of the nozzle by particle agglomerates and inability to produce particles in the submicron range. Particles formed in the nanometer size range by existing techniques all show poor control of particle size distribution as well as poor crystallinity resulting in poor physical stability (recrystallization and particle growth). Furthermore, the use of exotic solvents like DMSO as well as emulsifiers which have limited use in large scale production have been used to obtain sub-micron particles.

The object of the present invention is to overcome the drawbacks entailing methods and devices according to prior art. More specifically the object is to obtain particles of higher quality regarding size distribution, surface structure and morphology and to allow formation of articles of a size that up to know haven't been possible or only with difficulty, i.e. particles of a size less than 1 µm.

SUMMARY OF THE INVENTION

In the first aspect of the invention the object has been achieved in that a device of the kind specified in the preamble of claim 1 includes the specific features that the device includes a first part having a first wall and a second part having a second wall, the walls forming an interspace between each other, the mixing means being formed by the interspace and at least one of the walls is movable such that the width of the interspace is adjustable.

In operation a solution containing the substance flows through the first inlet means and the first conduit means and reaches the mixing means as a liquid jet. The atomizing agent flows through the second inlet means and the second conduit means and reaches the mixing means as a jet.

Due to the large angle between the two jets a cross-shear action takes place through which the jet of the atomizing agent cuts the liquid jet of the solution or suspension into small droplets by which the particles are formed. The cross-shear action diminishes the risk for clogging and thereby results in a narrow range for the size of the obtained particles. By adequate setting of pressure and velocity the particles obtained can be as small as about 0.2-0.3 µm or even down to 0.05 µm. The cross-shear action also results in a relatively smooth surface structure of the particles.

By providing the mixing means in an interspace between the walls the particle creation is effective and well controlled. By the possibility to adjust the width of the interspace the device can be adapted to different kinds of substances solvents or atomising agents or to various conditions in other respect. A very important effect of this feature is that clogging can be cooped with by widening the width of the interspace.

According to a preferred embodiment the second inlet means is adapted for a gaseous atomizing agent. Thereby a gaseous medium can be used as the atomizing agent which in many cases is the most effective medium for obtaining the small particles from the solution/suspension.

According to an alternative preferred embodiment the second inlet means is adapted for a liquid atomizing agent. Thereby a liquid medium can be used as the atomizing agent. When using a liquid it should be selected to match the solution/suspension in the way that it will have anti-solvent properties in relation to the solution/suspension. For certain applications the use of liquid as atomizing agent has particular advantages.

According to a further preferred embodiment the second inlet means is adapted for an atomizing agent in the supercritical stage. Using a supercritical medium has proven to be very effective for this function.

According to a further preferred embodiment of the invented device the angle is about 90°.

The cross-shear action described above is more effective the larger the angle is and is optimized when reaching 90°.

According to a further preferred embodiment the outlet means is aligned with the second conduit means.

By the aligned arrangement of these conduit means the risk for clogging is further reduced and disturbances due to changes of direction are eliminated.

According to a further preferred embodiment the second inlet means includes a straight elongated portion, the centre of which defines a centre axis of the device, and the second conduit means includes an end section connected to the mixing means, the end section having a direction forming an angle to the axis of the device of at least 30°, preferably at least 45°.

This arrangement allows on one hand an injection of the atomizing agent into the device which injection is concentrated and easy to control and on the other hand a possibility to optimize the distribution of this agent to the mixing means for obtaining the cross-shear action.

According to a further preferred embodiment the angle between the direction of the end section and the axis is about 90°.

Also in this case the conditions for the intersecting jets are better the larger this angle is and is optimized when the angle is 90°.

According to a further preferred embodiment the end section is at last partly defined by two planar walls.

This allows a well controlled establishment of an effective and stable gas jet of the atomizing agent when reaching the mixing means. The flow resistance is minimized and this embodiment also has constructional advantages.

According to a further preferred embodiment the end section has an angular extension of 360° around said axis.

By arranging the end section completely circumferentially a homogeneous and harmonious jet stream is obtained. The output is maximized in relation to given dimension and the rotational symmetry achieved is advantageous for cooping with the dynamic forces created during operation.

According to a further preferred embodiment the first conduit means has an end portion connected to said mixing means, said end portion extending in a direction of which the main component is axial.

This is a constructively advantageous and simple arrangement for achieving the desired angle between the two jets when meeting at the mixing means.

According to a further preferred embodiment the direction of the end section is substantially radial and the direction of said end portion is substantially axial.

Thereby the two jets meet each other at substantially a right angle in an geometrically simple and advantageous arrangement.

According to a further preferred embodiment the end portion is constituted by an elongated slot.

Thereby the liquid jet coming from the end portion will be of elongated nature allowing a more distributed mixing. This increases the possible output from the device of given dimensions.

According to a further preferred embodiment the elongated slot forms a closed loop around the axis of the device, preferably a circular slot.

This is a particularly advantageous when the end section of the second conduit means has an angular extension of 360°. Thereby the mixing means is established as a closed loop, in the preferred case as a circle. This will further contribute to the advantages obtained with the mentioned 360°-arrangement and mentioned above.

According to a further preferred embodiment said end portion terminates in one of said walls.

This is a simple construction for arranging the entrance of the liquid jet into the mixing means.

According to a further preferred embodiment the movable wall is urged towards the other wall by biasing means, preferably a mechanical spring.

The width of the end section thereby will be determined by the pressure force from the medium within the end portion on one hand and the counter-acting force from the biasing means on the other hand. Should clogging occur the pressure will rise and thereby widen this width against the action of the biasing force so that the clogged particles are ejected, whereafter the pressure falls and the width returns to its normal state. By this embodiment the risk for clogging problem is further reduced.

According to a further preferred embodiment the first and second inlet means are coaxial, the second inlet means enclosing the first inlet means.

The coaxial arrangement contributes to a simple and robust construction and allows an advantageous localisation of the conduit means so as to achieve an efficient cross-shearing of the jets at the mixing means.

According to a further preferred embodiment the second conduit means includes a chamber in which the second inlet means terminates.

By such a chamber the operation becomes more controlled since the chamber contributes to maintain a stable pressure for creating the gaseous jet towards the mixing means. The chamber also minimizes risk for disturbance due to required change of direction from the inlet means to the direction of the end section of the second conduit means.

According to a further preferred embodiment the device includes a first part through which the first and second inlet means extend and a second part through which the first inlet means and the first conduit means extend, which first and second parts form an interspace between each other, which interspace constitutes the second conduit means, the mixing means and the outlet means.

Thereby a constructional simple device is achieved and wherein the flow paths can be formed in an advantageous pattern.

The above described preferred embodiments of the inverted device are specified in the claims dependent from claim 1.

In the second aspect of the invention the object has been achieved in that a method of the kind defined in the preamble of claim 22 includes the specific step that the jets are supplied to a mixing area formed by an interspace located between a first wall on a first part of a device and a second wall on a second part of the device, the width of the interspace being adjustable.

By the invented method advantages corresponding to those gained by the invented device are achieved, which advantages are described above.

Preferred embodiments of the invented method are specified in the claims dependent from claim 22. Through these preferred embodiments corresponding advantages are achieved as described above for some embodiments of the invented device.

The invented device and method are particularly useful for producing particles of a size below 10 µm and in particular below 3 µm since better quality can be obtained for such particles according to the invention, as explained above. Furthermore the invention makes it possible to obtain particles of a size below 1 µm, down to about 0.2 µm and even down to 0.05 µm.

Therefore the present invention also relates to a use of the invented device or the invented method for forming particles of that size.

The need for particles of high quality and of the size discussed above is particularly accentuated in the pharmaceutical area, e.g. for administrating a pharmaceutical by inhalation.

Therefore the present invention also relates to a use of the invented device or the invented method for forming particles of a pharmaceutical substance.

The invention will be explained more in detail by the description of advantageous examples of embodiments of the invention below and with reference to the accompanying drawings.

DETAILED DESCRIPTION OF ADVANTAGEOUS EXAMPLES

Figure 1:
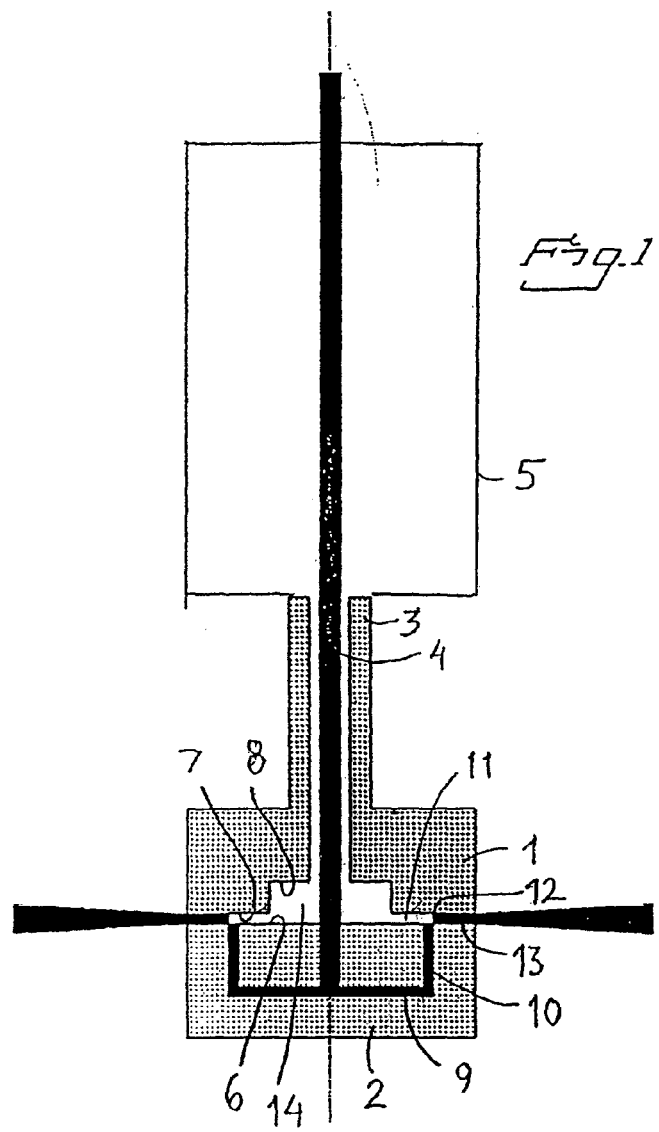
FIG. 1 is a schematic cross section through a first example of an embodiment of the invention.

In FIG. 1 a first embodiment of the invention is schematically depicted in a cross section.

The device consists of an upper part 1 and a lower part 2 as the main components. The upper part 1 is by a pipe 3 connected to a vessel 5 containing $CO_2$ under high pressure. Coaxially with and inside the pipe 3 another pipe 4 is arranged. The inner pipe 4 is connected to a source of a solution containing the substance from which the particles are to be formed. The solution can be based e.g. on acetone, isopropanol, methanol, ethanol or water. The solution is fed through the pipe 4 at high pressure.

Although carbondioxide due to its relatively low cost, toxicity, flammability a critical temperature is preferred other fluids such as nitrous oxide, sulphur hexafluoride, xenon, ethylene, propane, chlorotrifluormerthane, ethane, helium, neon and trifluoromethan can be applied in the process.

The two parts 1,2 are arranged closed to each other but with a small interspace between them and having a respective planar surface 6,7 facing each other.

In the planar surface 7 of the upper part 1 a recess 8 is formed coaxial with the pipes 3 and 4, by which recess a chamber 14 is created.

The inner pipe 4 extends through the chamber 9 and into the lower part 2 and communicates with a disc-shaped cavity 9 in the lower part 2. The outer periphery of the cavity 9 is in communication with a cylindrical cavity 10 in the lower part 2. The cylindrical cavity terminates in the planar wall 6 of the lower part. The lower part 2 thus is formed by two separate portions since the cavities 9,10 completely separate an inner portion from an outer portion of this part.

In operation the solution containing the substance is supplied through the inner pipe 4 which thus forms inlet means for the solution. Via the conduit means constituted by the cavities 9 and 10 the solution flows to the interspace between the two parts 1,2.

The $CO_2$ is supplied from the vessel 5 through the outer pipe 3 to the cavity 14 from where it flows through a conduit means 11 formed by the interspace between the two planar surfaces 6,7 to the area where the cavity 10 terminates.

Thus a gas jet of $CO_2$ from the cavity 10 and a liquid jet of the solution meet each other at 90° where the cavity 10 terminates, which area here is called the mixing means 12. The $CO_2$ is preferably but not necessarily supplied at supercritical state.

It should be apparent that the gas jet is disc shaped and thus extends in 360° and that the liquid jet is shaped as a circular band in cross section.

When the two jets meet each other in the mixing means 12 the gas jet breaks down the liquid jet into very small droplets.

From the mixing means 12 the droplets flow in a jet stream radially outwards between the outer portion of the interspace between the planar walls 6,7 and leaves the interspace in solid form. The solid particles are obtained either by the dissolution of the solution. If a suspension is used the particles are extracted there from. This outer portion thus functions as an outlet means 13 for the particles.

Figure 2:
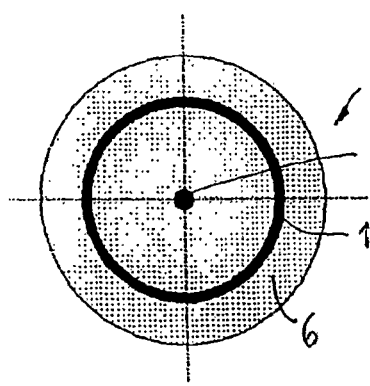
FIG. 2 is a top view of a detail of FIG. 1.

FIG. 2 is a top view of the lower part 2 illustrating the circular cavity 10 terminating in the planar surface 6, and the centrally arranged pipe 4.

Figure 3:
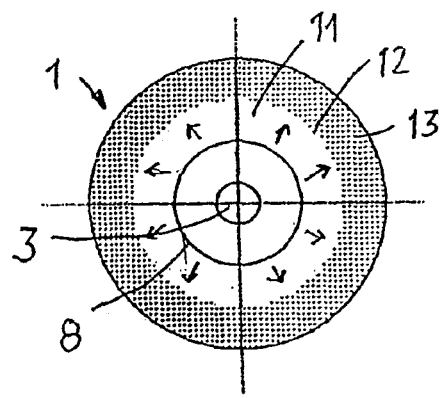
FIG. 3 is a bottom view of another detail of FIG. 1.

FIG. 3 is a bottom view of the upper part 2 showing the recess 8 in the planar wall 7 and the pipe 3 terminating therein. The outer region of the wall 7 surface is shaded in the figure representing the area outside the mixing means 12, i.e. the region forming the outlet means 13 for the particles. Radially inside the mixing means 12 is the area where the gas is present and establishes a 360° jet stream as represented by the arrows.

Figure 4:
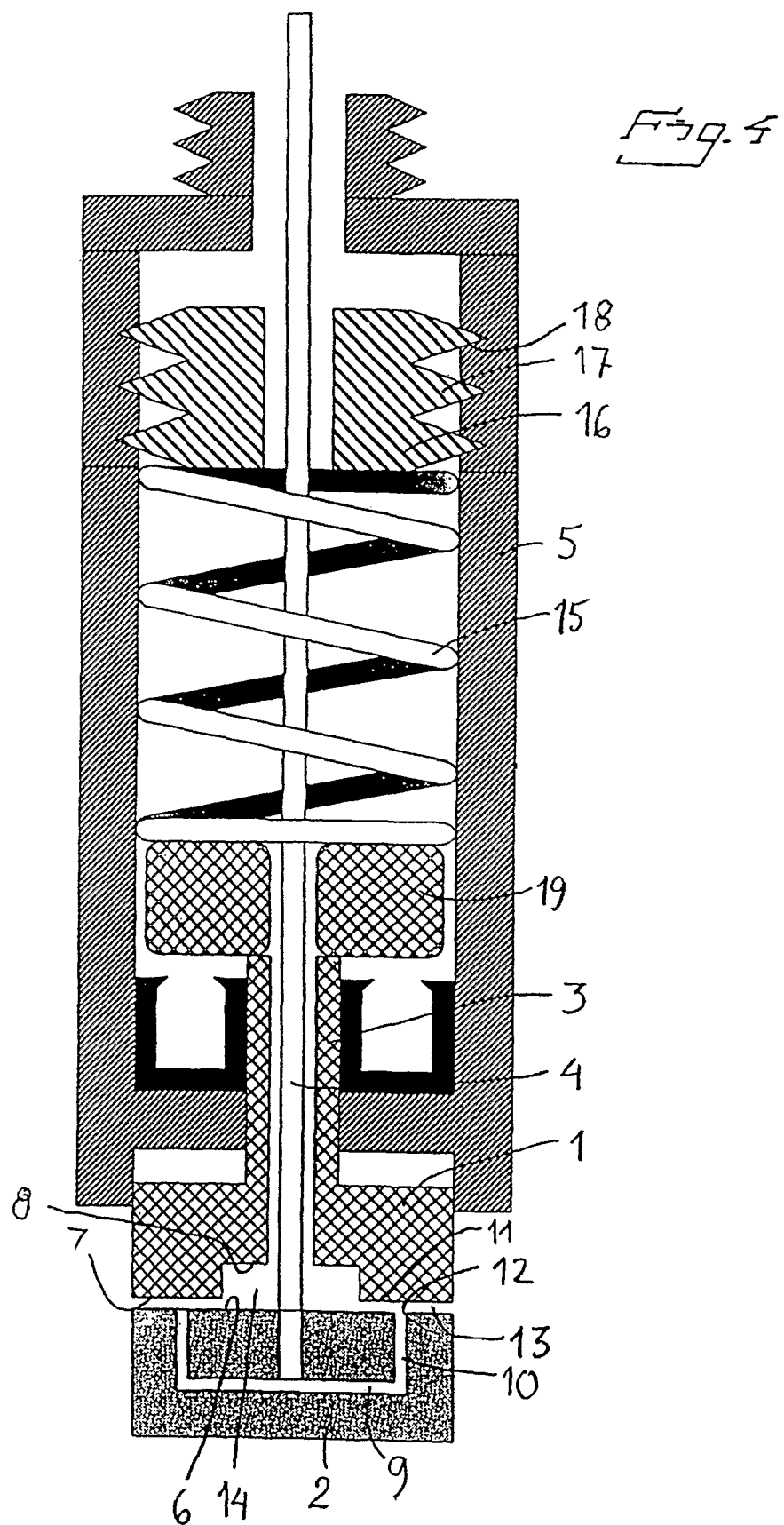
FIG. 4 is a schematic cross section through a second example of an embodiment of the invention.

FIG. 4 is a section through a second example of an embodiment of the invention. The main components are similar to those of FIG. 1 and have the same reference numbers.

In this example the upper part 1 together with he outer pipe 3 is movable arranged. In the pressure vessel 5 for the $CO_2$ gas a helical spring 15 is provided. The spring rests at its upper end against a support 16, the position of which can be axially adjusted by means of a thread 17 cooperating with a female thread 18 in the internal wall of the vessel 5. The lower end of the spring contacts a body 19, which abuts the upper end of the outer pipe 3.

By the spring 15 the upper part 1 via the body 19 and the outer pipe 3 is urged downwards. The spring force thus tends to press the two parts 1 and 2 together, whereas the pressure from the $CO_2$ gas within the interspace between the planar surfaces 6 and 7 and within the chamber 14 tends to press the parts 1, 2 away from each other.

The spring force can be adjusted by adjusting the position of the support 16 so that under normal operating the spring force and the force from the gas pressure are equalised at a certain width of the interspace. Typically he spring force corresponds to a pressure within the interspace of about 25 atm.

Should clogging occur in the mixing means 12 the outflow from the outlet 13 becomes restricted and the pressure in the region radially inside the mixing means will consequently increase. The increased pressure rises the upper part 1 against the action of the spring 15 so that the width of the interspace increases. The increased width allows the clogged particles to be pressed out by the gas pressure resulting in a pressure chop. Thereby the spring force will press down the upper part 1 to its normal position and the process can continue.

In the device illustrated in FIGS. 1-3 the diameter of the pipe 4 is about 0.5 mm and the diameter of the pipe 3 is about 0.7 mm, leaving a clearance between the pipes of about 0.1 mm. The cavity 14 has a depth of about 2 mm and a diameter of about 4 mm. The diameter of the cylindrical conduit is about 5 mm and the width of the distance between the surfaces 6, 7 is about 0.1 mm.

Figure 5:
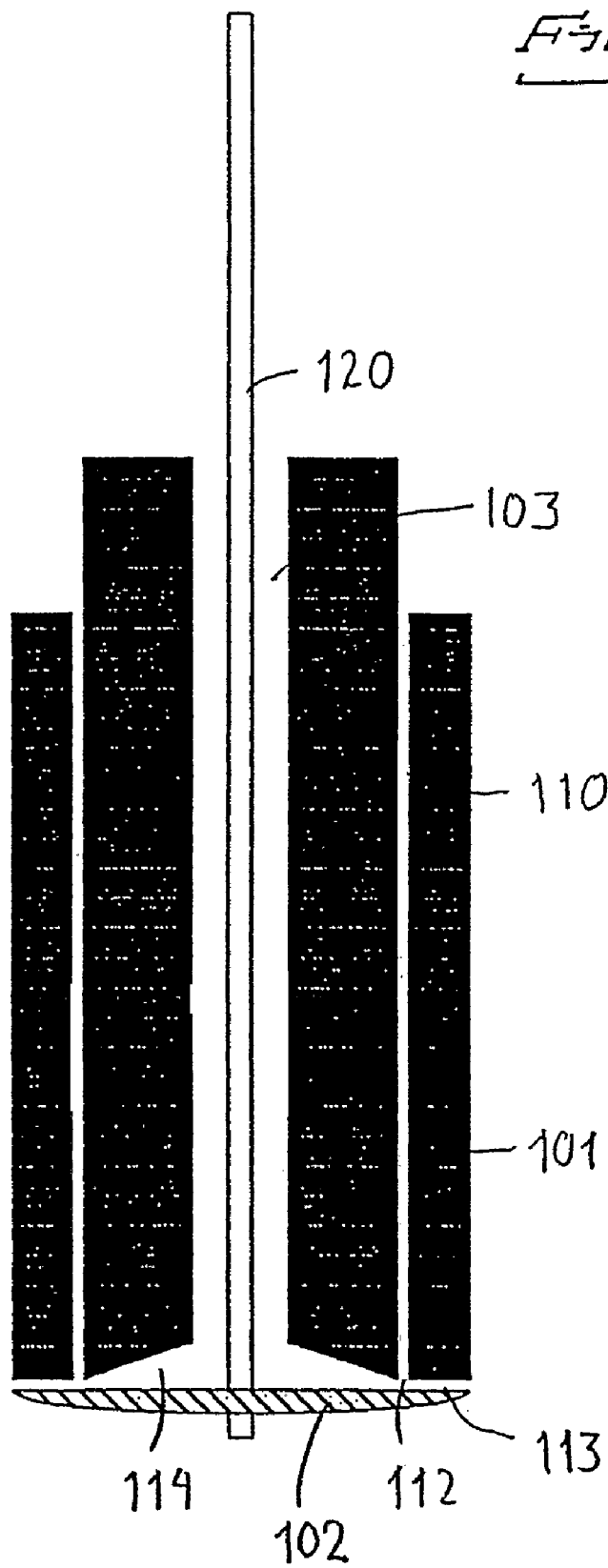
FIG. 5 is a schematic cross section through a third example of an embodiment of the invention.

In FIG. 5 an alternative configuration of the device is illustrated. In this example the solution is fed through the channel 110 in the upper part 101. In cross-section the channel 110 has the shape of a circular band. Through the channel 103 $CO_2$ is supplied and is fed to the mixing means 112 via a conical chamber 114. A disc 102 forms a lower part of the device and the position of the disc 102 can be adjusted by the rod 120. A small clearance is formed between the upper part 101 and the disc 102 which clearance constitutes the outlet 113 of the device.

As an alternative the atomizing agent can be a liquid. This should be an anti-solvent for the liquid used in the solution/suspension. Thus if for example the latter is water the liquid atomizing agent can be acetone and vice versa.

EXAMPLE 1

Budesonide was used as the model substance which ahs low molecular weight and is crystalline. Acetone (analytical grade) and liquid $CO_2$ with 99.99% purity were used as solvent and supercritical antisolvent, respectively. Different concentrations of budesonide solution were prepared before each experimental run.

Budesonide with concentration (1% W/v) in acetone was used for reproducibility of the process. A Jasco 880-PU HPLC pump feeds the solution of the substance to the device by pipe 4 which connected to the lower part. Liquid $CO_2$ was cooled down to −9° C. and the delivered by a THAR Design pump into 100 ml particle formation vessel (TharDesign) through a T-fitting to vessel 5 and upper part. A water bath and a Jasco 880-81 back-pressure regulator were used to control the temperature at 60 degrees C. and the pressure 100 bar inside the particle formation vessel respectively. The flow rate of anti-solvent CO2 was 18 g/min and the flow rate of solution of Budesonide was 0.2 ml/min. When the all solution was pumped the delivery of the solution into the vessel is stopped and $CO_2$ pumped for draying powder. The all system was depressurized and the particles were collected.

The recrystallised powders have been characterised by X-ray diffraction (XRD) and scanning electron microscopy (SEM). X-ray powder diffraction reveal no change in cristallinity as compared with the starting material. The SEM pictures of the starting material and the processed material was clearly showed that the particles formed by the nozzle according to the invention were in the nanometer size range and uniform in shape.

In a series of three duplicating experiments using the same conditions as in Example 1 resulted in particles with the same size range and same crystallinity demonstrating the reproducibility of the process.

EXAMPLE 2

In this experiment the flow rate of the solution system was varied: 0.2, 0.6, 1.2 ml/min with the rest of the test conditions as in the first experiment. Here the particle size and morphology are similar to those in the first experiment according to SEM pictures.

EXAMPLE 3

The same test substance Budesonide was crystallized from isopropanol (2% W/v) using the same conditions as in Example 1 but with slightly higher flow rate of the vehicle system, 0.3 ml/min. Isopropanol influenced particle morphology with well-formed particles in the range of 1-2 micrometer.

EXAMPLE 4

In this example Budesonide concentration was 1.25% W/v and crystallized from acetone using same temperature and pressure conditions as in Example 1. The flow rate of vehicle system was 1.5 ml/min and the antisolvent CO2 flow rate was 100 g/min. Here the particle size was according to SEM pictures 200 nanometer.

The invention claimed is:

1. A device for formation of small particles of a certain substance, the device comprising
    first inlet means for a solution or a suspension containing the substance,
    second inlet means for an atomizing agent, wherein the first and the second inlet means are coaxial,
    mixing means for mixing said solution/suspension and said atomizing agent,
    outlet means for the particles,
    first conduit means from the first inlet means to the mixing means, and
    second conduit means from the second inlet means to the mixing means, which first and second conduit means meet each other at the mixing means at an angle of at least 30°, wherein the device comprises a first part having a first wall and a second part having a second wall, the walls forming an interspace between each other, said mixing means being formed by said interspace and at least one of said walls is movable such that a width of said interspace is adjustable.

2. A device according to claim 1, wherein said at least one movable wall is movable to and from the other wall.

3. A device according to claim 2, wherein said movable wall is urged towards the other wall by biasing means.

4. A device according to claim 3, wherein said biasing means is a mechanical spring.

5. A device according to claim 1, wherein said first and second inlet means extend through the first part and the first inlet means and the first conduit means extend through said second part.

6. A device according to claim 1, wherein said interspace constitutes the second conduit means, the mixing means and the outlet means.

7. A device according to claim 1, wherein the second inlet means includes a straight elongated portion, the center of which defines a center axis of the device and said second conduit means includes an end section connected to the mixing means, the end section forming an angle of at least 30° to the axis of the device.

8. A device according to claim 7, wherein said end section at least partly is defined by said first and second walls.

9. A device according to claim 8, wherein said walls are planar walls.

10. A device according to claim 7, wherein said end section has an angular extension of 360° around said axis.

11. A device according to claim 7, wherein said first conduit means has an end portion connected to said mixing means, said end portion extending in a direction of which a main component is axial.

12. A device according to claim 7, wherein a direction of said end section is substantially radial and a direction of said end portion is substantially axial.

13. A device according to claim 11, wherein said end portion is constituted by an elongated slot.

14. A device according to claim 13, wherein said elongated slot forms a closed loop.

15. A device according to claim 11, wherein said end portion terminates in one of said walls.

16. A device according to claim 1, wherein said outlet means is aligned with said second conduit means.

17. A device according to claim 1, wherein the second inlet means encloses the first inlet means.

18. A device according to claim 1, wherein said second conduit means includes a chamber in which the second inlet means terminates.

19. A method for formation of small particles of a certain substance, the method comprising:
    providing a first inlet means for a solution or a suspension containing the substance,
    providing a second inlet means for an atomizing agent, wherein the first and the second inlet means are coaxial,
    supplying a jet of the atomizing agent from the second inlet means to a mixing area,
    supplying a liquid jet of the solution or the suspension containing the substance from the first inlet means to the mixing area, and
    withdrawing a jet of said particles from the mixing area,
the jet of the atomizing agent and the liquid jet being supplied such that they meet each other in the mixing area at an angle in the range of 30° to 150°, wherein said jets are supplied to a mixing area formed by an interspace located between a first wall on a first part of a device and a second wall of a second part of the device and wherein the width of said interspace is adjustable.

20. A method according to claim 19, wherein said supplying said jet of said atomizing agent to said mixing area is performed by supplying a gaseous jet.

21. A method according to claim 19, wherein said supplying said jet of said atomizing agent to said mixing area is performed by supplying a liquid jet.

22. A method according to claim 19, wherein said supplying said jet of said atomizing agent to said mixing area is performed by supplying a medium at supercritical state.

23. A method according to claim 19, wherein said angle is about 90°.

24. A method according to claim 19, wherein the jet of the atomizing agent is supplied and the particle jet is withdrawn in such a way that these jets are substantially aligned.

25. A method according to claim 19, wherein the atomizing agent is supplied to a cavity from which said jet of an atomizing agent is created.

26. A method according to claim 25, wherein a jet of the atomizing agent of 360° is created.

27. A method according to claim 19, wherein the jet of the solution/suspension is created to form an elongated jet.

28. A method according to claim 27, wherein the solution/suspension jet is created to form a closed loop.

29. A method according to claim 19, further comprising forming said particles of a size in the range of 0.05-10 μm.

30. A method according to claim 19, wherein said supplying said liquid jet of said solution or said suspension containing the substance to the mixing area is a supplying of a solution or suspension containing a pharmaceutical substance.

31. A device according to claims 1, configured to form said particles of a size in the range of 0.05-10 μm.

32. A device according to claim 1, wherein the second inlet means is connected to a source of an atomizing agent.

33. A device according to claim 1, wherein the first inlet means encloses the second inlet means.

* * * * *